United States Patent
Xu et al.

(10) Patent No.: US 11,312,999 B2
(45) Date of Patent: Apr. 26, 2022

(54) SET OF GENES FOR MOLECULAR CLASSIFYING OF MEDULLOBLASTOMA AND USE THEREOF

(71) Applicant: HANGZHOU CANHELP GENOMICS TECHNOLOGY CO. LTD., Hangzhou (CN)

(72) Inventors: Qinghua Xu, Hangzhou (CN); Chengshu Chen, Hangzhou (CN); Yifeng Sun, Hangzhou (CN); Jinying Chen, Hangzhou (CN); Qifeng Wang, Hangzhou (CN); Kaibin Song, Hangzhou (CN)

(73) Assignee: HANGZHOU CANHELP GENOMICS TECHNOLOGY CO. LTD., Hangzhou (CN)

( * ) Notice: Subject to any disclaimer, the term of this patent is extended or adjusted under 35 U.S.C. 154(b) by 0 days.

(21) Appl. No.: 17/271,215

(22) PCT Filed: Sep. 6, 2019

(86) PCT No.: PCT/CN2019/104613
§ 371 (c)(1),
(2) Date: Feb. 25, 2021

(87) PCT Pub. No.: WO2020/048518
PCT Pub. Date: Mar. 12, 2020

(65) Prior Publication Data
US 2021/0254179 A1  Aug. 19, 2021

(30) Foreign Application Priority Data
Sep. 7, 2018 (CN) .......................... 201811043820.3

(51) Int. Cl.
*C12P 19/34* (2006.01)
*C12Q 1/6886* (2018.01)
*C12Q 1/6806* (2018.01)
*C12Q 1/6837* (2018.01)

(52) U.S. Cl.
CPC ......... *C12Q 1/6886* (2013.01); *C12Q 1/6806* (2013.01); *C12Q 1/6837* (2013.01)

(58) Field of Classification Search
CPC .................................................. C12Q 1/6886
See application file for complete search history.

(56) References Cited

U.S. PATENT DOCUMENTS

| 2007/0148666 A1 | 6/2007 | Rajeev | |
| 2015/0359855 A1* | 12/2015 | Carney | .............. A61K 41/0038 604/20 |
| 2016/0017318 A1 | 1/2016 | Asgharzadeh et al. | |

FOREIGN PATENT DOCUMENTS

| CN | 108728533 A | 11/2018 |
| CN | 109182517 A | 1/2019 |
| WO | 2012044921 A1 | 4/2012 |

OTHER PUBLICATIONS

Wanqing Chen, et al. Cancer statistics in China, 2015, Ca Cancer J Clin, 2016, pp. 115-132, vol. 66 No. 2.
David W. Ellison, et al., Medulloblastoma: clinicopathological correlates of SHH, WNT, and non-SHH/WNT molecular subgroups, Acta Neuropathol., 2011, pp. 381-396, vol. 121 No. 3.
Paul A. Northcott, et al., Rapid, reliable, and reproducible molecular sub-grouping of clinical medulloblastoma samples, Acta Neuropathol, 2012, pp. 615-626, vol. 123, No. 4.
Sambrook, et al., Molecular Cloning: Laboratory Manual, 1989, New York: Cold Spring Harbor Laboratory Press.
Yilin He, et al., Research Progress of Molecular Subtypes Of Medulloblastoma. Chin J Pathol, 2015, pp. 357-360, vol. 44 No. 5.
Jing Zhang, et al., Accuracy analysis of identifying molecular subtypes of children and adolescents with medulloblastoma using real-time fluorescence quantitative PCR, Chin J Neurosurg, 2016, pp. 867-972, vol. 32 No. 9.
David N. Louis, et al., The 2016 World Health Organization Classification of Tumors of the Central Nervous System: a summary, Acta Neuropathol, 2016.
Junjie Jing, et al., Molecular Typing of Medulloblastoma, Chinese Journal of Neurosurgical Disease Research, 2013, pp. 547-549, vol. 12 No. 6, China Academic Journal Electronic Publishing House.

* cited by examiner

*Primary Examiner* — Kenneth R Horlick
(74) *Attorney, Agent, or Firm* — Bayramoglu Law Offices LLC

(57) ABSTRACT

A set of genes for the molecular classifying of medulloblastoma is disclosed, including the following 24 genes: EPHA7 gene, OTX2 gene, ROBO1 gene, TTR gene, LGR5 gene, IGF2BP3 gene, TBR1 gene, ZFPM2 gene, TRDC gene, TRAC gene, PEX5L gene, NKD1 gene, RALYL gene, GABRA5 gene, GAD1 gene, TNC gene, KCNA1 gene, EOMES gene, MAB21L2 gene, WIF1 gene, DKK2 gene, PDLIM3 gene, IMPG2 gene, and KHDRBS2 gene. In addition, the present invention also discloses the use of the genome in the preparation of a kit and a gene chip for the molecular classifying of medulloblastoma. After validation, the present invention can accurately differentiate medulloblastoma WNT subgroup, SHE subgroup, Group3 subgroup, and Group4 subgroup, and has important clinical significance for the precise treatment of patients due to the objective results, high accuracy, and short experimental period.

8 Claims, 2 Drawing Sheets
Specification includes a Sequence Listing.

SEQUENCE LISTING

```
<160> NUMBER OF SEQ ID NOS: 72

<210> SEQ ID NO 1
<211> LENGTH: 22
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers
```

<400> SEQUENCE: 1
ggagaaggca ctgtggttat ag                                              22

<210> SEQ ID NO 2
<211> LENGTH: 21
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 2
ggtttcaggg tcaatgtagg t                                               21

<210> SEQ ID NO 3
<211> LENGTH: 21
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 3
agggtgcagg tatggtttaa g                                               21

<210> SEQ ID NO 4
<211> LENGTH: 21
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 4
cgagctggag atgtcttctt t                                               21

<210> SEQ ID NO 5
<211> LENGTH: 20
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 5
ttccgtggtc attcccttc                                                  20

<210> SEQ ID NO 6
<211> LENGTH: 22
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 6
gaactgaggc tcactcttta cc                                              22

```
<210> SEQ ID NO 7
<211> LENGTH: 22
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 7
ccatcacaga agtccactca tt                                        22

<210> SEQ ID NO 8
<211> LENGTH: 20
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 8
gccagcctca gacacaaata                                           20

<210> SEQ ID NO 9
<211> LENGTH: 22
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 9
tcttcaccaa ctgcatccta aa                                        22

<210> SEQ ID NO 10
<211> LENGTH: 23
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 10
ggactaccac cagaaggata aac                                       23

<210> SEQ ID NO 11
<211> LENGTH: 21
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 11
gggaggtgct ggatagttta c                                         21

<210> SEQ ID NO 12
<211> LENGTH: 24
```

```
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 12
ctagcttggt ccttactgga atag                                          24

<210> SEQ ID NO 13
<211> LENGTH: 21
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 13
ggtttcccac ttctcctcaa t                                             21

<210> SEQ ID NO 14
<211> LENGTH: 22
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 14
gcctatgaac agacacctat cc                                            22

<210> SEQ ID NO 15
<211> LENGTH: 20
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 15
gctccaacca gtgggaaata                                               20

<210> SEQ ID NO 16
<211> LENGTH: 22
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 16
gctgcatgtg atgagcaata aa                                            22

<210> SEQ ID NO 17
<211> LENGTH: 20
<212> TYPE: DNA
<213> ORGANISM: Artificial Sequence
<220> FEATURE:
<223> OTHER INFORMATION: the sequence is synthetized
```

```
<220> FEATURE:
<221> NAME/KEY: misc_feature
<223> OTHER INFORMATION: Primers

<400> SEQUENCE: 17
ccctgaactg cctgtatgaa                                               20

<210> SEQ ID NO 18
<211> LENGTH: 20
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 18
tcagaaccct ggcgaataag                                               20

<210> SEQ ID NO 19
<211> LENGTH: 23
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 19
caactggatc ctacccgaat tta                                           23

<210> SEQ ID NO 20
<211> LENGTH: 21
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 20
gcagtgacaa gcagcaataa g                                             21

<210> SEQ ID NO 21
<211> LENGTH: 23
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 21
gttccacctg agtggagaat tta                                           23

<210> SEQ ID NO 22
<211> LENGTH: 22
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers
```

<400> SEQUENCE: 22
gaggcggttc catagtgaat ag          22

<210> SEQ ID NO 23
<211> LENGTH: 22
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 23
gtgcctgtaa tctcagctac tc          22

<210> SEQ ID NO 24
<211> LENGTH: 22
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 24
ggagtacagt ggtgcaatct ta          22

<210> SEQ ID NO 25
<211> LENGTH: 21
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 25
cgcctggaga agattgagaa a          21

<210> SEQ ID NO 26
<211> LENGTH: 22
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 26
acacacattc ctcttggatc ag          22

<210> SEQ ID NO 27
<211> LENGTH: 21
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 27
gaatagggag ccggtgataa a          21

```
<210> SEQ ID NO 28
<211> LENGTH: 22
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 28
gacctctcct tggtaccatt tc                                              22

<210> SEQ ID NO 29
<211> LENGTH: 22
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 29
tgcagagaca ccttgaagta tg                                              22

<210> SEQ ID NO 30
<211> LENGTH: 22
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 30
cattctccag ctaggccaat aa                                              22

<210> SEQ ID NO 31
<211> LENGTH: 23
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 31
ctctggcctc tacaccattt atc                                             23

<210> SEQ ID NO 32
<211> LENGTH: 20
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 32
tgcgtctcag gaacacaatc                                                 20

<210> SEQ ID NO 33
<211> LENGTH: 23
<212> TYPE: DNA
```

```
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 33
cctggagact tgagttctga ttt                                              23

<210> SEQ ID NO 34
<211> LENGTH: 22
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 34
cctggagaag gacttgctat tg                                               22

<210> SEQ ID NO 35
<211> LENGTH: 20
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 35
gtggcaaagc cgacaataac                                                  20

<210> SEQ ID NO 36
<211> LENGTH: 22
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 36
ccgaatgaaa tctcctgtct ca                                               22

<210> SEQ ID NO 37
<211> LENGTH: 19
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 37
cctcctgcac cttccattt                                                   19

<210> SEQ ID NO 38
<211> LENGTH: 22
<212> TYPE: DNA
<213> ORGANISM: Artificial Sequence
<220> FEATURE:
<223> OTHER INFORMATION: the sequence is synthetized
<220> FEATURE:
```

```
<221> NAME/KEY: misc_feature
<223> OTHER INFORMATION: Primers

<400> SEQUENCE: 38
aacttctctt ccacgctgat ag                                              22

<210> SEQ ID NO 39
<211> LENGTH: 23
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 39
cctggattct atggagtgaa ctg                                             23

<210> SEQ ID NO 40
<211> LENGTH: 21
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 40
tctagtcctg gagggcaaat a                                               21

<210> SEQ ID NO 41
<211> LENGTH: 22
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 41
cgcatttgat tgcttccagt ta                                              22

<210> SEQ ID NO 42
<211> LENGTH: 21
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 42
acgcctcagg acagaaatta g                                               21

<210> SEQ ID NO 43
<211> LENGTH: 22
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 43
```
cctttggtca tcaccaggat ta                                                    22

<210> SEQ ID NO 44
<211> LENGTH: 20
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 44
tgtcccaaag ccgtcaatag                                                       20

<210> SEQ ID NO 45
<211> LENGTH: 22
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 45
cctatcctca gcatcccttc ta                                                    22

<210> SEQ ID NO 46
<211> LENGTH: 22
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 46
ggaaagctca ctgctctcat ac                                                    22

<210> SEQ ID NO 47
<211> LENGTH: 20
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 47
gcctgtggtc tccacataaa                                                       20

<210> SEQ ID NO 48
<211> LENGTH: 22
<212> TYPE: DNA
<213> ORGANISM: Artificial Sequence
<220> FEATURE:
<223> OTHER INFORMATION: the sequence is synthetized
<220> FEATURE:
<221> NAME/KEY: misc_feature
<223> OTHER INFORMATION: Primers

<400> SEQUENCE: 48
gccaacagta cagagggaaa ta                                                    22

```
<210> SEQ ID NO 49
<211> LENGTH: 24
<212> TYPE: DNA
<213> ORGANISM: Artificial Sequence
<220> FEATURE:
<223> OTHER INFORMATION: the sequence is synthetized

<400> SEQUENCE: 49
tgaccaagaa ggcgatgaag agct                                          24

<210> SEQ ID NO 50
<211> LENGTH: 24
<212> TYPE: DNA
<213> ORGANISM: Artificial Sequence
<220> FEATURE:
<223> OTHER INFORMATION: the sequence is synthetized

<400> SEQUENCE: 50
tctgctgttg ttgctgttgt tggc                                          24

<210> SEQ ID NO 51
<211> LENGTH: 24
<212> TYPE: DNA
<213> ORGANISM: Artificial Sequence
<220> FEATURE:
<223> OTHER INFORMATION: the sequence is synthetized

<400> SEQUENCE: 51
atccgataca gtgtggaagt ggca                                          24

<210> SEQ ID NO 52
<211> LENGTH: 24
<212> TYPE: DNA
<213> ORGANISM: Artificial Sequence
<220> FEATURE:
<223> OTHER INFORMATION: the sequence is synthetized

<400> SEQUENCE: 52
ttggcaggat ggcttctcat cgtc                                          24

<210> SEQ ID NO 53
<211> LENGTH: 25
<212> TYPE: DNA
<213> ORGANISM: Artificial Sequence
<220> FEATURE:
<223> OTHER INFORMATION: the sequence is synthetized

<400> SEQUENCE: 53
cctgtggctt tcttgtcctt ctcct                                         25

<210> SEQ ID NO 54
<211> LENGTH: 24
<212> TYPE: DNA
<213> ORGANISM: Artificial Sequence
<220> FEATURE:
<223> OTHER INFORMATION: the sequence is synthetized

<400> SEQUENCE: 54
ttcacttgct cacagctctc cacc                                          24

<210> SEQ ID NO 55
<211> LENGTH: 26
<212> TYPE: DNA
<213> ORGANISM: Artificial Sequence
<220> FEATURE:
<223> OTHER INFORMATION: the sequence is synthetized
```

<400> SEQUENCE: 55
aggtgtttgg gtggattctc cttagc                                          26

<210> SEQ ID NO 56
<211> LENGTH: 27
<212> TYPE: DNA
<213> ORGANISM: Artificial Sequence
<220> FEATURE:
<223> OTHER INFORMATION: the sequence is synthetized

<400> SEQUENCE: 56
tgttgaactg gatatcacat agccggc                                         27

<210> SEQ ID NO 57
<211> LENGTH: 26
<212> TYPE: DNA
<213> ORGANISM: Artificial Sequence
<220> FEATURE:
<223> OTHER INFORMATION: the sequence is synthetized

<400> SEQUENCE: 57
tggtacaagc aacttcccag caaaga                                          26

<210> SEQ ID NO 58
<211> LENGTH: 24
<212> TYPE: DNA
<213> ORGANISM: Artificial Sequence
<220> FEATURE:
<223> OTHER INFORMATION: the sequence is synthetized

<400> SEQUENCE: 58
ttgctgaaga gctgccaaac actg                                            24

<210> SEQ ID NO 59
<211> LENGTH: 23
<212> TYPE: DNA
<213> ORGANISM: Artificial Sequence
<220> FEATURE:
<223> OTHER INFORMATION: the sequence is synthetized

<400> SEQUENCE: 59
tgccttaact gttcggccag agg                                             23

<210> SEQ ID NO 60
<211> LENGTH: 24
<212> TYPE: DNA
<213> ORGANISM: Artificial Sequence
<220> FEATURE:
<223> OTHER INFORMATION: the sequence is synthetized

<400> SEQUENCE: 60
aatctctgcc tcccaggttc aagc                                            24

<210> SEQ ID NO 61
<211> LENGTH: 24
<212> TYPE: DNA
<213> ORGANISM: Artificial Sequence
<220> FEATURE:
<223> OTHER INFORMATION: the sequence is synthetized

<400> SEQUENCE: 61
tgcttcttct gagcttctgc ctcc                                            24

<210> SEQ ID NO 62
<211> LENGTH: 24

```
<212> TYPE: DNA
<213> ORGANISM: Artificial Sequence
<220> FEATURE:
<223> OTHER INFORMATION: the sequence is synthetized

<400> SEQUENCE: 62
actcccaaac tccaagacag ccat                                              24

<210> SEQ ID NO 63
<211> LENGTH: 24
<212> TYPE: DNA
<213> ORGANISM: Artificial Sequence
<220> FEATURE:
<223> OTHER INFORMATION: the sequence is synthetized

<400> SEQUENCE: 63
aatcgaggat gacctgtgcg aacc                                              24

<210> SEQ ID NO 64
<211> LENGTH: 24
<212> TYPE: DNA
<213> ORGANISM: Artificial Sequence
<220> FEATURE:
<223> OTHER INFORMATION: the sequence is synthetized

<400> SEQUENCE: 64
agcgcctcag ccttatcacc attc                                              24

<210> SEQ ID NO 65
<211> LENGTH: 24
<212> TYPE: DNA
<213> ORGANISM: Artificial Sequence
<220> FEATURE:
<223> OTHER INFORMATION: the sequence is synthetized

<400> SEQUENCE: 65
attgggagtg tgttcgtggg tgag                                              24

<210> SEQ ID NO 66
<211> LENGTH: 27
<212> TYPE: DNA
<213> ORGANISM: Artificial Sequence
<220> FEATURE:
<223> OTHER INFORMATION: the sequence is synthetized

<400> SEQUENCE: 66
acccagagtc tcctaatact ggttccc                                           27

<210> SEQ ID NO 67
<211> LENGTH: 24
<212> TYPE: DNA
<213> ORGANISM: Artificial Sequence
<220> FEATURE:
<223> OTHER INFORMATION: the sequence is synthetized

<400> SEQUENCE: 67
cgctcagtgt aggtgagtgc cttc                                              24

<210> SEQ ID NO 68
<211> LENGTH: 24
<212> TYPE: DNA
<213> ORGANISM: Artificial Sequence
<220> FEATURE:
<223> OTHER INFORMATION: the sequence is synthetized

<400> SEQUENCE: 68
```

```
aaagcaggtg gttgagcagt ttgc                                           24

<210> SEQ ID NO 69
<211> LENGTH: 24
<212> TYPE: DNA
<213> ORGANISM: Artificial Sequence
<220> FEATURE:
<223> OTHER INFORMATION: the sequence is synthetized

<400> SEQUENCE: 69
ttgcagaact tcctgtcctg gtgg                                           24

<210> SEQ ID NO 70
<211> LENGTH: 24
<212> TYPE: DNA
<213> ORGANISM: Artificial Sequence
<220> FEATURE:
<223> OTHER INFORMATION: the sequence is synthetized

<400> SEQUENCE: 70
ctgccaacct gtgtcctgga gatg                                           24

<210> SEQ ID NO 71
<211> LENGTH: 24
<212> TYPE: DNA
<213> ORGANISM: Artificial Sequence
<220> FEATURE:
<223> OTHER INFORMATION: the sequence is synthetized

<400> SEQUENCE: 71
ttggtgggct gagcagagaa gaaa                                           24

<210> SEQ ID NO 72
<211> LENGTH: 30
<212> TYPE: DNA
<213> ORGANISM: Artificial Sequence
<220> FEATURE:
<223> OTHER INFORMATION: the sequence is synthetized

<400> SEQUENCE: 72
tctagggata actgctcatg attactccca                                     30
```

SET OF GENES FOR MOLECULAR CLASSIFYING OF MEDULLOBLASTOMA AND USE THEREOF

CROSS REFERENCE TO THE RELATED APPLICATIONS

This application is the national phase entry of International Application No. PCT/CN2019/104613, filed on Sep. 6, 2019, which is based upon and claims priority to Chinese Patent Application No. 201811043820.3, filed on Sep. 7, 2018, the entire contents of which are incorporated herein by reference.

TECHNICAL FIELD

The present invention relates to the field of cancer diagnosis and molecular biology, as well as the clinical application of the diagnostic techniques. Specifically, the present invention relates to a set of genes for the molecular classifying of medulloblastoma and their use. By establishing the molecular classifying model of medulloblastoma and detecting the expression level of the signature genes in the medulloblastoma tissue, medulloblastoma subgroups, including WNT subgroup, SHE subgroup (Sonic Hedgehog subgroup), Group3 subgroup, and Group4 subgroup, can be identified. In addition, the present invention also relates to a kit for the molecular classifying of medulloblastoma.

BACKGROUND

China Cancer Statistics showed that the number of new cases of cancer of the brain and central nervous system (CNS) in China reached about 101,600 and has been listed as the seventh of the top ten most common cancers in 2015, with a death toll of 61,000 and a mortality rate of 60% (Chen W, Zheng R, Baade P D, et al. Cancer statistics in China, 2015[J]. Ca Cancer J Clin, 2016, 66(2):115-132). Medulloblastoma is the most common malignant brain tumor in children and is a primitive neuroectodermal tumor mainly occurring in the cerebellum. Approximately 85 percent of medulloblastomas occur in children younger than 18 years of age, and one in five children with brain tumors has a medulloblastoma. The current strategy of combining surgery with chemoradiotherapy has resulted in an overall 5-year survival rate of more than 50%. However, molecular targeted therapy and individualized precision therapy have attracted the most attention in the field of medulloblastoma research due to the serious impact on the life quality of children and their families due to intellectual damage caused by high-dose radiotherapy.

With the rapid development of molecular biology techniques, researchers have discovered that medulloblastoma is not a single disease, but a brain tumor composed of several different molecular subgroups. Currently, there are four recognized core molecular subgroups of medulloblastoma: WNT subgroup, SHH subgroup (Sonic Hedgehog subgroup), Group3 subgroup, and Group4 subgroup. These subgroups differ in terms of treatment and prognosis and correspond to different clinical strategies. The further in-depth discussion regarding the molecular classifying of medulloblastoma has an important significance on the study of the pathogenesis of medulloblastoma, the development of the clinical trials, the targeted therapy drugs research and the development, as well as the clinical improvement of the individualized treatment plan, and eventually reach the purpose of not only improving the survival rate of children with severe diseases but also improving the life quality in the patient group with good prognosis.

TABLE 1

Subgroups and morbidity of medulloblastoma

| Subgroups | WNT subgroup | SHH subgroup | Group 3 subgroup | Group 4 subgroup |
|---|---|---|---|---|
| Morbidity | 11% | 28% | 27% | 34% |

The tumor is a genomic disease, and the genomic changes play an important role in tumor genesis and development. In recent years with the rapid development of molecular biology and bioinformatics technology, researchers have used biochip and high-throughput sequencing technology to simultaneously measure the expression level of thousands of genes in tumor tissue, from which genes related to tumor subgroups and specific expression patterns were found. Domestic and foreign-related studies have reported that gene expression profile analysis can assist in elucidating the nature of the tumor and accurately classifying tumors at the molecular level. According to WHO "Classification of tumors of the central nervous system" (2016), the gene expression profile analysis is the gold standard for the molecular classifying of medulloblastoma and is also the best method to differentiate four different subgroups (Ellison D W, Dalton J, Kocak M, et al. Medulloblastoma: clinicopathological correlates of SHH, WNT, and non-SHH/WNT molecular subgroups. Acta neuropathologica. 2011; 121(3): 381-396. doi:10.1007/s00401-011-0800-8).

However, this approach requires a large amount of high-quality RNA extracted from fresh-frozen tumor samples for genome-wide transcriptional microarrays analysis. This approach is impractical in the current clinical setting due to the difficulty to obtain the fresh tissue samples and the complicated and expensive experimental operation (Pilin He, Qing Chang, Progress in the study of molecular classifying of medulloblastoma [J]. Chin J Pathol, 2015, 44(5): 357-360). In the United States, Northcott et al. developed a molecular sub-grouping assay based on paraffin embedded samples using NanoString nCounter Technology platform (Northcott P A, Shih Djh, Remke M, et al. Rapid, reliable, and reproducible molecular sub-grouping of clinical medulloblastoma samples. Acta Neuropathologica. 2012; 123 (4): 615-626. The doi: 10.1007/s00401-011-0899-7). In 84 paraffin embedded tissue samples, 57 samples were accurately differentiated by this assay, and the classifying accuracy was only 68%. Therefore, this assay is susceptible to be interfered with by RNA degradation in paraffin embedded tissue samples. Meanwhile, the NanoString nCounter Technology is a closed technology platform and not suited for large-scale clinical applications due to specific detection equipment, the reagent, and the consumable materials, high cost of running and maintenance, and complex experimental operation procedure.

SUMMARY

A technical problem to be solved in the present invention is to provide a set of genes for the molecular classifying of medulloblastoma, to establish a statistical analysis model of medulloblastoma, and to aid patients to achieve the individualized treatment.

A second technical problem to be solved in the present invention is to provide the use of a set of genes for the molecular classifying of medulloblastoma.

A third technical problem to be solved in the present invention is to provide a kit for the molecular classifying of medulloblastoma and use thereof.

A fourth technical problem to be solved in the present invention is to provide the use of a set of genes for the molecular classifying of medulloblastoma for the preparation of a gene chip for identifying the subgroups of medulloblastoma.

To resolve the above technical problems, the present invention adopts the following technical solutions:

In one aspect, the present invention provides a set of genes for the molecular classifying of medulloblastoma, comprising the following 13 genes: EPHA7 gene, OTX2 gene, ROBO1 gene, TTR gene, LGR5 gene, IGF2BP3 gene, TBR1 gene, ZFPM2 gene, TRDC gene, TRAC gene, PEX5L gene, NKD1 gene, and RALYL gene.

The Gene ID of EPHA7 used herein is 2045, and the Accession No. in GenBank database is Nm_001288629.1.

The Gene ID of OTX2 used herein is 5015, and the Accession No. in GenBank database is NM_001270525.1.

The Gene ID of ROBO1 used herein is 6091, and the Accession No. in GenBank database is NM_001145845.1.

The Gene ID of TTR used herein is 7276, and the Accession No. in GenBank database is NM_000371.3.

The Gene ID of LGR5 used herein is 8549, and the Accession No. in GenBank database is NM_001277226.1.

The Gene ID of IGF2BP3 used herein is 10643, and the Accession No. in GenBank database is NM_006547.2.

The Gene ID of TBR1 used herein is 10716, and the Accession No. in GenBank database is NM_006593.3.

The Gene ID of ZFPM2 used herein is 23414, and the Accession No. in GenBank database is NM_012082.3.

The Gene ID of TRDC used herein is 28526, and it is a fusion gene.

The Gene ID of TRAC used herein is 28755, and it is a fusion gene.

The Gene ID of PEX5L used herein is 51555, and the Accession No. in GenBank database is NM_001256750.1.

The Gene ID of NKD1 used herein is 85407, and the Accession No. in GenBank database is NM_033119.4.

The Gene ID of RALYL used herein is 138046, and the Accession No. in GenBank database is NM_001100391.2.

As a preferred technical solution, the set of genes for the molecular classifying of medulloblastoma, also comprise the following 11 genes: GABRA5 gene, GAD1 gene, TNC gene, KCNA1 gene, EOMES gene, MAB21L2 gene, WIF1 gene, DKK2 gene, PDLIM3 gene, IMPG2 gene, and KHDRBS2 gene.

The Gene ID of GABRA5 used herein is 2558, and the Accession No. in GenBank database is NM_001165037.1.

The Gene ID of GAD1 used herein is 2571, and the Accession No. in GenBank database is NM_000817.2.

The Gene ID of TNC used herein is 3371, and the Accession No. in GenBank database is NM_002160.3.

The Gene ID of KCNA1 used herein is 3736, and the Accession No. in GenBank database is NM_000217.2.

The Gene ID of EOMES used herein is 8320, and the Accession No. in GenBank database is NM_001278182.1.

The Gene ID of MAB21L2 used herein is 10586, and the Accession No. in GenBank database is NM_006439.4.

The Gene ID of WIF1 used herein is 11197, and the Accession No. in GenBank database is NM_007191.4.

The Gene ID of DKK2 used herein is 27123, and the Accession No. in GenBank database is NM_014421.2.

The Gene ID of PDLIM3 used herein is 27295, and the Accession No. in GenBank database is NM_001114107.4.

The Gene ID of IMPG2 used herein is 50939, and the Accession No. in GenBank database is NM_016247.3.

The Gene ID of KHDRBS2 used herein is 202559, and the Accession No. in GenBank database is NM_001350622.1.

As a preferred technical solution, the molecular subgroups of medulloblastoma are WNT subgroup, SHH subgroup, Group3 subgroup, and Group4 subgroup.

As a preferred technical solution, the genes were screened by the following methods: selecting the gene combinations with high specificity to medulloblastoma by using the analysis technique of "big data and algorithm drive"; firstly building medulloblastoma gene expression profile database, containing 20,250 genes known to mankind, 461 samples, approximately 10 million data points; correlating more than 20,000 human gene expression data in each sample with the clinical data of the samples, and then screening specific medulloblastoma genes through a statistical analysis method variance test, that is, analyzing the relevance of each gene to medulloblastoma molecular subgroups, and extracting the genes with the highest correlation as signature genes, eventually obtaining 24 genes for constructing classifying model.

The present invention establishes a gene-marker combination model through the joint application of gene detection, marker combination, and data mining algorithm, and uses a multi-gene prediction model to differentiate four subgroups of medulloblastoma, including WNT subgroup, SHH subgroup, Group3 subgroup, and Group4 subgroup. It mainly comprises the following steps:

(1) Firstly, building medulloblastoma gene expression profile database, containing 20,250 genes known to mankind, 461 samples, about 10 million data points; correlating and matching more than 20,000 human gene expression data in each sample with the clinical data of the samples;

(2) Screening specific genes for medulloblastoma through the statistical analysis method variance test, that is, analyzing the relevance of each gene to medulloblastoma molecular subgroups, and extracting the genes with the highest correlation as signature genes, eventually obtaining 24 genes closely related to each subgroup of medulloblastoma, which are EPHA7 gene, OTX2 gene, ROBO1 gene, TTR gene, LGR5 gene, IGF2BP3 gene, TBR1 gene, ZFPM2 gene, TRDC gene, TRAC gene, PEX5L gene, NKD1 gene, and RALYL gene, GABRA5 gene, GAD1 gene, TNC gene, KCNA1 gene, EOMES gene, MAB21L2 gene, WIF1 gene, DKK2 gene, PDLIM3 gene, IMPG2 gene, and KHDRBS2 gene, respectively.

(3) Detecting the expression level of the above 24 genes, then establishing a statistical analysis model by using Support Vector Machine for the molecular classifying of medulloblastoma. For each sample to be tested, calculating the Similarity Score between the 24 genes' expression pattern of the sample and each subgroup of medulloblastoma in the database. According to the rule of the highest Similarity Score, determining the molecular subgroup belongs to the sample.

The present invention provides a detection method for identifying the subgroups of medulloblastoma, including the following steps:

(1) Contacting the biological samples from patients with medulloblastoma with biomarkers that including the above-mentioned 24 genes; the biological samples are in-vitro tumor tissue from the objects and may be fresh samples or formalin-fixed paraffin embedded (FFPE) samples.

On this basis, performing a further identification of the subgroups of medulloblastoma:

(2) Detecting the expression patterns and the levels of 24 genes in biological samples and determining the subgroups of biological samples based on the expression levels. Calculating the Similarity Score between biological samples and each subgroup of medulloblastoma by using the data analysis method. According to the rule of the highest Similarity Score, the subgroup was identified. The detection involves the isolation of RNA from the samples, the RNA was used for polymerase chain reaction (PCR), the PCR is reverse transcription PCR (RT-PCR), optionally with real-time RT-PCR or the gene chip or high-throughput sequencing technology.

In a second aspect, the present invention provides the use of a set of genes for the molecular classifying of medulloblastoma for the preparation of a kit for the molecular classifying of medulloblastoma.

In a third aspect, the present invention provides a kit for the molecular classifying of medulloblastoma, wherein the kit comprises the following biomarkers, the biomarkers are selected from any one or more of the genes for the molecular classifying of medulloblastoma.

As a preferred technical solution, the biomarkers are nucleic acids, oligonucleotide chains, or PCR primer sets.

As a preferred technical solution, the PCR primer sets comprise:
  EPHA7 gene: the forward primer is as set forth in SEQ ID NO. 1, and the reverse primer is as set forth in SEQ ID NO. 2;
  OTX2 gene: the forward primer is as set forth in SEQ ID NO. 3, and the reverse primer is as set forth in SEQ ID NO. 4;
  ROBO1 gene: the forward primer is as set forth in SEQ ID NO. 5, and the reverse primer is as set forth in SEQ ID NO. 6;
  TTR gene: the forward primer is as set forth in SEQ ID NO. 7, and the reverse primer is as set forth in SEQ ID NO. 8;
  LGR5 gene: the forward primer is as set forth in SEQ ID NO. 9, and the reverse primer is as set forth in SEQ ID NO. 10;
  IGF2BP3 gene: the forward primer is as set forth in SEQ ID NO. 11, and the reverse primer is as set forth in SEQ ID NO. 12;
  TBR1 gene: the forward primer is as set forth in SEQ ID NO. 13, and the reverse primer is as set forth in SEQ ID NO.14;
  ZFPM2 gene: the forward primer is as set forth in SEQ ID NO. 15, and the reverse primer is as set forth in SEQ ID NO. 16;
  TRDC gene: the forward primer is as set forth in SEQ ID NO. 17, and the reverse primer is as set forth in SEQ ID NO. 18;
  TRAC gene: the forward primer is as set forth in SEQ ID NO. 19, and the reverse primer is as set forth in SEQ ID NO. 20;
  PEX5L gene: the forward primer is as set forth in SEQ ID NO. 21, and the reverse primer is as set forth in SEQ ID NO. 22;
  NKD1 gene: the forward primer is as set forth in SEQ ID NO. 23, and the reverse primer is as set forth in SEQ ID NO. 24;
  RALYL gene: the forward primer is as set forth in SEQ ID NO. 25, and the reverse primer is as set forth in SEQ ID NO. 26.

As a preferred technical solution, the PCR primer sets also comprise:
  GABRA5 gene: the forward primer is as set forth in SEQ ID NO. 27, and the reverse primer is as set forth in SEQ ID NO. 28;
  GAD1 gene: the forward primer is as set forth in SEQ ID NO. 29, and the reverse primer is as set forth in SEQ ID NO. 30;
  TNC gene: the forward primer is as set forth in SEQ ID NO. 31, and the reverse primer is as set forth in SEQ ID NO. 32;
  KCNA1 gene: the forward primer is as set forth in SEQ ID NO. 33, and the reverse primer is as set forth in SEQ ID NO. 34;
  EOMES gene: the forward primer is as set forth in SEQ ID NO. 35, and the reverse primer is as set forth in SEQ ID NO. 36;
  MAB21L2 gene: the forward primer is as set forth in SEQ ID NO. 37, and the reverse primer is as set forth in SEQ ID NO. 38;
  WIF1 gene: the forward primer is as set forth in SEQ ID NO. 39, and the reverse primer is as set forth in SEQ ID NO. 40;
  DKK2 gene: the forward primer is as set forth in SEQ ID NO. 41, and the reverse primer is as set forth in SEQ ID NO. 42;
  PDLIM3 gene: the forward primer is as set forth in SEQ ID NO. 43, and the reverse primer is as set forth in SEQ ID NO. 44;
  IMPG2 gene: the forward primer is as set forth in SEQ ID NO. 45, and the reverse primer is as set forth in SEQ ID NO. 46;
  KHDRBS2 gene: the forward primer is as set forth in SEQ ID NO. 47, and the reverse primer is as set forth in SEQ ID NO. 48.

The use of the above-mentioned kit includes the following steps:
(1) Contacting the biological samples containing the tumor tissue with the biomarkers;
(2) Determining the expression level of the markers in the biological samples;
(3) Detecting the gene expression patterns in biological samples and comparison with the gene expression profile database of medulloblastoma.

The kit can detect the expression by real-time quantitative reverse transcription polymerase chain reaction (RT-PCR), or by the gene chips, or by high-throughput sequencing techniques.

The expression level detected by the kit is the mRNA expression level.

Only as a supplementary example of the above-mentioned in the present invention, for the paraffin embedded medulloblastoma tissues, the real-time quantitative reverse transcription polymerase chain reaction (RT-PCR) is used to differentiate the subgroups of medulloblastoma, which includes the following steps:
(1) Obtaining the paraffin embedded medulloblastoma tissues;
(2) Detecting the expression of 24 genes in the sample through real-time quantitative reverse transcription polymerase chain reaction;
(3) Detecting the expression patterns of 24 genes in the sample and comparison with the gene expression profile data of medulloblastoma to differentiate the subgroups of medulloblastoma.

In a fourth aspect, the present invention provides the use of the kit for the preparation of a formulation for identifying the subgroups of medulloblastoma.

In a fifth aspect, the present invention provides the use of a set of genes for the molecular classifying of medulloblastoma for the preparation of a gene chip for identifying the subgroups of medulloblastoma, wherein the gene chip comprises a solid phase carrier and a probe, wherein the probe is hybridized with the 13 gene sequences to be tested and/or their complementary sequences, wherein the 13 genes are EPHA7 gene, OTX2 gene, ROBO1 gene, TTR gene, LGR5 gene, IGF2BP3 gene, TBR1 gene, ZFPM2 gene, TRDC gene, TRAC gene, PEX5L gene, NKD1 gene, and RALYL gene; wherein the probe is as set forth in SEQ ID NO. 49-SEQ ID NO. 61, respectively.

In a sixth aspect, the present invention provides the use of a set of genes for the molecular classifying of medulloblastoma for the preparation of a gene chip for identifying the subgroups of medulloblastoma, wherein the gene chip comprises a solid phase carrier and a probe, wherein the probe is hybridized with the 24 gene sequences to be tested and/or their complementary sequences, wherein the 24 genes are EPHA7 gene, OTX2 gene, ROBO1 gene, TTR gene, LGR5 gene, IGF2BP3 gene, TBR1 gene, ZFPM2 gene, TRDC gene, TRAC gene, PEX5L gene, NKD1 gene, and RALYL gene, GABRA5 gene, GAD1 gene, TNC gene, KCNA1 gene, EOMES gene, MAB21L2 gene, WIF1 gene, DKK2 gene, PDLIM3 gene, IMPG2 gene, and KHDRBS2 gene; wherein the probe is as set forth in SEQ ID NO. 49-SEQ ID NO. 72, respectively.

The present invention constructs a molecular classifying marker of medulloblastoma and differentiates the subgroups of medulloblastoma by detecting 24 genes related to medulloblastoma, namely, WNT subgroup, SHH subgroup, Group3 subgroup, and Group4 subgroup. The present invention can assist doctors in making clinical decisions and achieve precise medicine so as to improve the treatment effect and the life quality of the patients with medulloblastoma. After validation, the kit provided by the present invention can accurately differentiate the subgroups of medulloblastoma, namely, WNT subgroup, SHH subgroup, Group3 subgroup, and Group4 subgroup, and has an important clinical significance for the precise treatment of patients due to the wide range of application, high accuracy, and short experimental period.

Compared with the prior art (gene chip and NanoString), the beneficial effects of the present invention are as follows:

The present invention selects the gene combinations with high specificity to medulloblastoma by using the analysis technique of "big data and algorithm drive"; the inventors build the medulloblastoma gene expression profile database, containing 20,250 genes known to mankind, 461 samples, approximately 10 million data points; correlate more than 20,000 human gene expression data in each sample with the clinical data of the samples, and then screen the specific medulloblastoma genes through the statistical analysis method variance test, and analyze the relevance of each gene to medulloblastoma molecular subgroups, and extract the highest correlation genes as signature genes. Eventually, the inventors obtain 24 genes for constructing the classifying model. According to the general principles of machine learning, the 24 gene combinations are the most closely related to the occurrence of medulloblastoma among more than 20,000 genes known to humans, and therefore have good specificity.

Due to the good specificity of 24 gene combinations provided by the present invention, specific medulloblastoma gene expression can be detected through the trace amount of tumor cells in paraffin embedded tissue, and well overcome the interference of RNA degradation in paraffin tissue, complete testing through the classic two-step PCR (Reverse transcription+Amplification). The method provided by the present invention did not require fresh surgical samples and the testing platform such as gene chip and NanoString nCounter Technology which involve trivial experimental procedure and expensive testing. The present method can fully meet the requirements of the large-scale clinical popularization in our country due to wide scope, high accuracy, and low detection cost, and achieve an unexpected technical effect by existing methods.

After validation, the present invention can accurately differentiate medulloblastoma WNT subgroup, SHH subgroup, Group3 subgroup, and Group4 subgroup, and has an important clinical significance for the precise treatment of patients due to the objective results, high accuracy, and short experimental period.

To sum up, the inventors, through the creative work, provide a set of gene combinations for the molecular classifying of medulloblastoma and the detection kits thereof. The present invention is of the advantages of good specificity, high accuracy of detection, variable application range, and low detection cost, which can better meet the urgent clinical needs for the molecular classifying of medulloblastoma.

DETAILED DESCRIPTION OF THE EMBODIMENTS

Figure 1:
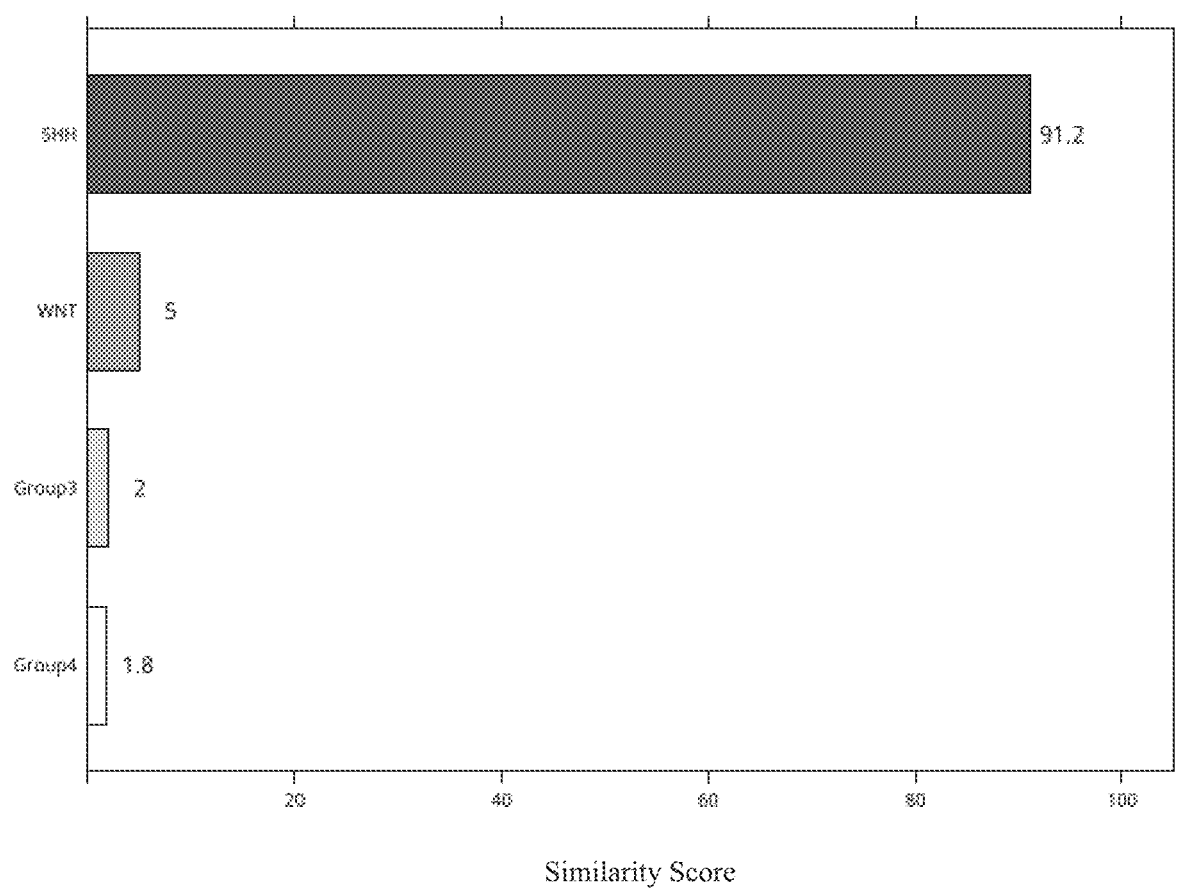
FIG. 1 is a schematic diagram of the medulloblastoma identification results of 24 genes in Example 6 of the present invention.

The present invention will be further described by reference to the following examples, which are illustrative only and are not intended to limit the present invention. The experimental methods without specific conditions in examples are conducted based on the conditions recommended by the manufacturer of the kit or based on the conventional experimental conditions, such as described by Sambrook et al., Molecular Cloning: Laboratory Manual (New York: Cold Spring Harbor Laboratory Press, 1989). Unless otherwise defined, all professional and scientific terms used herein shall have the same meanings familiar to skilled personnel in the field. In addition, any methods and materials similar to or equal to the recorded content may be applied to the present invention. The better examples and materials described in the present invention are only for demonstration purposes.

Example 1

Collection and Processing of Training Set Samples:

Firstly, the present invention analyzed the clinical data of 103 patients with medulloblastoma and the gene chip detection data of biological samples, including the relevant clinical data of 8 patients with WNT subgroup, 33 patients with SHE subgroup, 27 patients with Group3 subgroup, and 35 patients with Group4 subgroup, as well as the expression abundance data of 20,250 genes, then constructed the gene expression database of medulloblastoma.

Screening of 13 Specific Genes:

According to the test value of gene expression abundance, 13 genes closely related to the classifying of medulloblastoma were screened from 20,250 genes through the statistical analysis method variance test. These genes were differentially expressed in different subgroups of medulloblastoma. Therefore, they are of statistical significance (P<0.0001), as shown in Table 2.

TABLE 2

13 genes set

| Genes | Gene ID | Gene Description | P Value |
|---|---|---|---|
| EPHA7 | 2045 | EPH receptor A7 | <0.0001 |
| OTX2 | 5015 | orthodenticle homeobox 2 | <0.0001 |
| ROBO1 | 6091 | roundabout, axon guidance receptor, homolog 1 (*Drosophila*) | <0.0001 |
| TTR | 7276 | transthyretin | <0.0001 |
| LGR5 | 8549 | leucine-rich repeat containing G protein-coupled receptor 5 | <0.0001 |
| IGF2BP3 | 10643 | insulin-like growth factor 2 mRNA binding protein 3 | <0.0001 |
| TBR1 | 10716 | T-box, brain, 1 | <0.0001 |
| ZFPM2 | 23414 | zinc finger protein, FOG family member 2 | <0.0001 |
| TRDC | 28526 | T cell receptor delta constant | <0.0001 |
| TRAC | 28755 | T cell receptor alpha constant | <0.0001 |
| PEX5L | 51555 | peroxisomal biogenesis factor 5-like | <0.0001 |
| NKD1 | 85407 | naked cuticle homolog 1 (*Drosophila*) | <0.0001 |
| RALYL | 138046 | RALY RNA binding protein-like | <0.0001 |

Construction of the Statistical Analysis Model of 13 Genes:

Based on the expression patterns of 13 signature genes in 103 samples of medulloblastoma, the inventors established a statistical analysis model for the molecular classifying of medulloblastoma by using Support Vector Machine. For each sample to be tested, the model calculated the Similarity Score between the gene expression pattern of the sample and WNT subgroup, SHH subgroup, Group3 subgroup, and Group4 subgroup in the database, and identified the tumor subgroups of the sample according to the principle of the highest Similarity Score. Since its invention in 1992, the Support Vector Machine has been widely used to solve a variety of recognition problems, including financial data analysis, speech identification, and biological data analysis. The technicians in this field can use Support Vector Machine with open source, free analysis software, such as R, Rapid-Miner, and WEKA. Not limited to Support Vector Machine, other informed data mining methods can be used, such as Weighted Voting, k-Nearest Neighbors, Random Forest, Correlation Coefficients, etc.

Example 2

Validation of High-Throughput Sequencing Data

In the Example, the inventors analyzed the high-throughput sequencing data of 73 patients with medulloblastoma, including 8 patients with WNT subgroup, 10 patients with SHH subgroup, 16 patients with Group 3 subgroup, and 39 patients with Group 4 subgroup. After identifying the subgroups of each sample in 13-gene statistical analysis model, and comparison with the clinical diagnosis results, the diagnostic concordance rate was 75.3%. With the SHH subgroup as the reference, the sensitivity of classifying is 100.0%, and the specificity of classifying is 93.7%, as shown in Table 3 and Table 4.

TABLE 3

Classifying results of 13-gene analysis model in 73 high-throughput sequencing data

| | | High-throughput sequencing data results | | | |
|---|---|---|---|---|---|
| | | Group 3 subgroup | Group 4 subgroup | SHH subgroup | WNT subgroup |
| Classifying results of 13-gene analysis model | Group 3 subgroup | 16 | 14 | 0 | 0 |
| | Group 4 subgroup | 0 | 25 | 0 | 0 |
| | SHH subgroup | 0 | 0 | 10 | 4 |
| | WNT subgroup | 0 | 0 | 0 | 4 |
| Sum | | 16 | 39 | 10 | 8 |

TABLE 4

Performance index of 13-gene analysis model in 73 high-throughput sequencing data

| | Sample Size | Sensitivity | Specificity |
|---|---|---|---|
| Group 3 subgroup | 16 | 100.0% | 75.4% |
| Group 4 subgroup | 39 | 64.1% | 100.0% |
| SHH subgroup | 10 | 100.0% | 93.7% |
| WNT subgroup | 8 | 50.0% | 100.0% |
| Sum | 73 | Diagnose concordance rate = 75.3% | |

Example 3

In this example, the inventors conducted the molecular classifying experiment on 285 medulloblastoma paraffin tissue samples, including 51 cases of SHH subgroup, 46 cases of Group3 subgroup, and 188 cases of Group4 subgroup. Medulloblastoma-rich areas were collected from formalin-fixed paraffin embedded tissues by hand scraping, and the total RNA was extracted. DNase treatment to ensure complete removal of genomic DNA contamination; the cDNA was obtained after reverse transcription. The gene expression level of 13 genes was measured by the real-time quantitative polymerase chain reaction (RTQ-PCR) in paraffin embedded tumor tissues. The Similarity Score between the gene expression pattern of the sample and medulloblastoma subgroups in the database was calculated by using the analysis model.

After identifying the subgroups of each sample in 13-gene statistical analysis model, and comparison with the clinical diagnosis results, the diagnostic concordance rate was 78.2%. With the SHH subgroup as the reference, the predicted sensitivity is 98.0%, and the specificity is 99.6%, as shown in Table 5 and Table 6.

TABLE 5

Classifying results and performance index of 13-gene
analysis model in 285 QPCR experimental data set

| | | Clinical diagnostic results | | |
|---|---|---|---|---|
| | | Group 3 subgroup | Group 4 subgroup | SHH subgroup |
| Classifying results of 13-gene analysis model | Group 3 subgroup | 42 | 54 | 1 |
| | Group 4 subgroup | 4 | 131 | 0 |
| | SHH subgroup | 0 | 1 | 50 |
| | WNT subgroup | 0 | 2 | 0 |
| Sum | | 46 | 188 | 51 |

TABLE 6

Performance index of 13-gene analysis model
in 285 QPCR experimental data set

| | Sample size | Sensitivity | Specificity |
|---|---|---|---|
| Group 3 subgroup | 46 | 91.3% | 77.0% |
| Group 4 subgroup | 188 | 69.7% | 95.9% |
| SHH subgroup | 51 | 98.0% | 99.6% |
| Sum | 285 | Diagnose concordance rate = 78.2% | |

Example 4

Screening of 24 Specific Genes

The inventors expanded the F-test screening criteria to a p-value less than 0.001, resulting in an additional 11 genes. These genes were expressed differently in each subgroup of medulloblastoma, and the difference was statistically significant, as showed in Table 7. The 11 genes were combined with 13 genes in Example 1 to form a set of 24 genes.

TABLE 7

11 genes set

| Gene | Gene ID | Gene Description | P value |
|---|---|---|---|
| GABRA5 | 2558 | gamma-aminobutyric acid (GABA) A receptor, alpha 5 | <0.001 |
| GAD1 | 2571 | glutamate decarboxylase 1 (brain, 67 kDa) | <0.001 |
| TNC | 3371 | tenascin C | <0.001 |
| KCNA1 | 3736 | potassium channel, voltage gated shaker related subfamily A, member 1 | <0.001 |
| EOMES | 8320 | eomesodermin | <0.001 |
| MAB21L2 | 10586 | mab-21-like 2 (*C. elegans*) | <0.001 |
| WIF1 | 11197 | WNT inhibitory factor 1 | <0.001 |
| DKK2 | 27123 | dickkopf WNT signaling pathway inhibitor 2 | <0.001 |
| PDLIM3 | 27295 | PDZ and LIM domain 3 | <0.001 |
| IMPG2 | 50939 | interphotoreceptor matrix proteoglycan 2 | <0.001 |
| KHDRBS2 | 202559 | KH domain containing, RNA binding, signal transduction associated 2 | <0.001 |

Construction of 24-Gene Statistical Analysis Model

Based on the expression patterns of 24 genes in 103 medulloblastoma samples, the inventors established a statistical analysis model for the molecular classifying of medulloblastoma by using the Support Vector Machine. For each sample to be tested, the model calculated the Similarity Score between the gene expression pattern of the sample and WNT subgroup, SHH subgroup, Group3 subgroup, and Group4 subgroup in the database, and identified the tumor subgroups of the sample according to the principle of the highest Similarity Score.

Example 5

Validation of High-Throughput Sequencing Data

In the example, the inventors analyzed the high-throughput sequencing data of 73 cases with medulloblastoma, including 8 cases with WNT subgroup, 10 cases with SHH subgroup, 16 cases with Group 3 subgroup, and 39 cases with Group 4 subgroup. After identifying the subgroups of each sample in 24-gene statistical analysis model, and comparison with the clinical diagnosis results, the diagnostic concordance rate was 91.8%. Compared with the diagnostic concordance rate of 75.3% of the 13-gene analysis model in Example 2, the diagnostic concordance rate of the 24-gene model was significantly increased from 75.3% to 91.8%, which was not expected by the technicians in this field, and the unexpected technical effect was achieved. With the SHH subgroup as the reference, the sensitivity of classifying is 100.0%, and the specificity of classifying is 100.0%, as shown in Table 8 and Table 9.

TABLE 8

Classifying results of 24-gene analysis model in 73
high-throughput sequencing data

| | | High-throughput sequencing data results | | | |
|---|---|---|---|---|---|
| | | Group 3 subgroup | Group 4 subgroup | SHH subgroup | WNT subgroup |
| Classifying results of 24-gene analysis model | Group 3 subgroup | 16 | 6 | 0 | 0 |
| | Group 4 subgroup | 0 | 33 | 0 | 0 |
| | SHH subgroup | 0 | 0 | 10 | 0 |
| | WNT subgroup | 0 | 0 | 0 | 8 |
| Sum | | 16 | 39 | 10 | 8 |

TABLE 9

Performance index of 24-gene analysis model in 73
high-throughput sequencing data

| | Sample size | Sensitivity | Specificity |
|---|---|---|---|
| Group 3 subgroup | 16 | 100.0% | 89.5% |
| Group 4 subgroup | 39 | 84.6% | 100.0% |
| SHH subgroup | 10 | 100.0% | 100.0% |
| WNT subgroup | 8 | 100.0% | 100.0% |
| Sum | 73 | diagnose concordance rate = 91.8% | |

Example 6

In this example, the inventors conducted the molecular classifying experiment on 285 medulloblastoma paraffin tissue samples, including 51 cases of SHH subgroup, 46 cases of Group3 subgroup, and 188 cases of Group4 subgroup. Medulloblastoma-rich areas were collected from formalin-fixed paraffin embedded tissue by hand scraping, and the total RNA was extracted. DNase treatment to ensure complete removal of genomic DNA contamination; the cDNA was obtained after reverse transcription. The gene expression level of 24 genes was measured by the real-time quantitative polymerase chain reaction (RTQ-PCR) in paraffin embedded tumor tissues. The Similarity Score between the gene expression pattern of the sample and medulloblastoma subgroups in the database was calculated by using the analysis model.

After identifying the subgroups of each sample in the 24-gene statistical analysis model and comparing them with the clinical diagnosis results, the diagnostic concordance rate was 96.5%. Compared with the diagnostic concordance rate of 78.2% of the 13-gene analysis model in Example 3, the diagnostic concordance rate of 24-gene model was significantly increased from 78.2% to 96.5%, which was not expected by the technicians in this field, and the unexpected technical effect was achieved. With the SHH subgroup as the reference, the predicted sensitivity is 100.0%, and the specificity is 98.7%, as shown in Table 10 and Table 11.

TABLE 10

Classifying results and performance index of 24-gene analysis model in 285 QPCR experimental data set

| | | Clinical diagnostic results | | |
|---|---|---|---|---|
| | | Group 3 subgroup | Group 4 subgroup | SHH subgroup |
| Classifying results of 24-gene analysis model | Group 3 subgroup | 44 | 5 | 0 |
| | Group 4 subgroup | 2 | 180 | 0 |
| | SHH subgroup | 0 | 3 | 51 |
| | WNT subgroup | 0 | 0 | 0 |
| Sum | | 46 | 188 | 51 |

TABLE 11

Performance index of 24-gene analysis model in 285 QPCR experimental data set

| | Sample size | Sensitivity | Specificity |
|---|---|---|---|
| Group 3 subgroup | 46 | 95.7% | 97.9% |
| Group 4 subgroup | 188 | 95.7% | 97.9% |
| SHH subgroup | 51 | 100.0% | 98.7% |
| Sum | 285 | diagnose concordance rate = 96.5% | |

The PCR primer sets of 24 genes are designed as follows:

EPHA7 gene: the forward primer is as set forth in SEQ ID NO. 1, and the reverse primer is as set forth in SEQ ID NO. 2;

OTX2 gene: the forward primer is as set forth in SEQ ID NO. 3, and the reverse primer is as set forth in SEQ ID NO. 4;

ROBO1 gene: the forward primer is as set forth in SEQ ID NO. 5, and the reverse primer is as set forth in SEQ ID NO. 6;

TTR gene: the forward primer is as set forth in SEQ ID NO. 7, and the reverse primer is as set forth in SEQ ID NO. 8;

LGR5 gene: the forward primer is as set forth in SEQ ID NO. 9, and the reverse primer is as set forth in SEQ ID NO. 10;

IGF2BP3 gene: the forward primer is as set forth in SEQ ID NO. 11, and the reverse primer is as set forth in SEQ ID NO. 12;

TBR1 gene: the forward primer is as set forth in SEQ ID NO. 13, and the reverse primer is as set forth in SEQ ID NO. 14;

ZFPM2 gene: the forward primer is as set forth in SEQ ID NO. 15, and the reverse primer is as set forth in SEQ ID NO. 16;

TRDC gene: the forward primer is as set forth in SEQ ID NO. 17, and the reverse primer is as set forth in SEQ ID NO. 18;

TRAC gene: the forward primer is as set forth in SEQ ID NO. 19, and the reverse primer is as set forth in SEQ ID NO. 20;

PEX5L gene: the forward primer is as set forth in SEQ ID NO. 21, and the reverse primer is as set forth in SEQ ID NO. 22;

NKD1 gene: the forward primer is as set forth in SEQ ID NO. 23, and the reverse primer is as set forth in SEQ ID NO. 24;

RALYL gene: the forward primer is as set forth in SEQ ID NO. 25, and the reverse primer is as set forth in SEQ ID NO. 26;

GABRA5 gene: the forward primer is as set forth in SEQ ID NO. 27, and the reverse primer is as set forth in SEQ ID NO. 28;

GAD1 gene: the forward primer is as set forth in SEQ ID NO. 29, and the reverse primer is as set forth in SEQ ID NO. 30;

TNC gene: the forward primer is as set forth in SEQ ID NO. 31, and the reverse primer is as set forth in SEQ ID NO. 32;

KCNA1 gene: the forward primer is as set forth in SEQ ID NO. 33, and the reverse primer is as set forth in SEQ ID NO. 34;

EOMES gene: the forward primer is as set forth in SEQ ID NO. 35, and the reverse primer is as set forth in SEQ ID NO. 36;

MAB21L2 gene: the forward primer is as set forth in SEQ ID NO. 37, and the reverse primer is as set forth in SEQ ID NO. 38;

WIF1 gene: the forward primer is as set forth in SEQ ID NO. 39, and the reverse primer is as set forth in SEQ ID NO. 40;

DKK2 gene: the forward primer is as set forth in SEQ ID NO. 41, and the reverse primer is as set forth in SEQ ID NO. 42;

PDLIM3 gene: the forward primer is as set forth in SEQ ID NO. 43, and the reverse primer is as set forth in SEQ ID NO. 44;

IMPG2 gene: the forward primer is as set forth in SEQ ID NO. 45, and the reverse primer is as set forth in SEQ ID NO. 46;

KHDRBS2 gene: the forward primer is as set forth in SEQ ID NO. 47, and the reverse primer is as set forth in SEQ ID NO. 48.

The probe sequences of 24 genes are as shown in Table 12:

TABLE 12

| No. | Genes | Probe sequences |
|---|---|---|
| 1 | EPHA7 | SEQ ID NO. 49 |
| 2 | OTX2 | SEQ ID NO. 50 |
| 3 | ROBO1 | SEQ ID NO. 51 |
| 4 | TTR | SEQ ID NO. 52 |
| 5 | LGR5 | SEQ ID NO. 53 |
| 6 | IGF2BP3 | SEQ ID NO. 54 |
| 7 | TBR1 | SEQ ID NO. 55 |
| 8 | ZFPM2 | SEQ ID NO. 56 |
| 9 | TRDC | SEQ ID NO. 57 |
| 10 | TRAC | SEQ ID NO. 58 |
| 11 | PEX5L | SEQ ID NO. 59 |
| 12 | NKD1 | SEQ ID NO. 60 |
| 13 | RALYL | SEQ ID NO. 61 |
| 14 | GABRA5 | SEQ ID NO. 62 |
| 15 | GAD1 | SEQ ID NO. 63 |
| 16 | TNC | SEQ ID NO. 64 |
| 17 | KCNA1 | SEQ ID NO. 65 |
| 18 | EOMES | SEQ ID NO. 66 |
| 19 | MAB21L2 | SEQ ID NO. 67 |
| 20 | WIF1 | SEQ ID NO. 68 |
| 21 | DKK2 | SEQ ID NO. 69 |
| 22 | PDLIM3 | SEQ ID NO. 70 |
| 23 | IMPG2 | SEQ ID NO. 71 |
| 24 | KHDRBS2 | SEQ ID NO. 72 |

As shown in FIG. 1, the Similarity Scores of SHH subgroup, WNT subgroup, Group 3 subgroup, and Group4s were 91.2, 5.0, 2.0, and 1.8, respectively. Because the similarity score of the SHH subgroup is the highest, the sample was determined to be the SHH subgroup, which is consistent with the clinical diagnosis.

Example 7

Clinical Study of Molecular Classifying to Evaluate Patient Prognosis

In the example, the inventors selected 142 medulloblastoma paraffin tissue samples from the Department of Neurosurgery, Huashan Hospital Affiliated to Fudan University in Shanghai from 2006 to 2015 for molecular classifying detection and evaluated the clinical significance of classifying results in assessing patient prognosis. This is a retrospective clinical study with the largest number of medulloblastoma patients and the longest follow-up period that has been published so far in China. Medulloblastoma-rich areas were collected from formalin-fixed paraffin embedded tissue by hand scraping, and the total RNA was extracted. DNase treatment to ensure complete removal of genomic DNA contamination; the cDNA was obtained after reverse transcription. The gene expression level of 24 genes was measured by the real-time quantitative polymerase chain reaction (RTQ-PCR) in paraffin embedded tumor tissues. The Similarity Score between the gene expression pattern of the sample and medulloblastoma subgroups in the database was calculated by using the analysis model.

Figure 2:
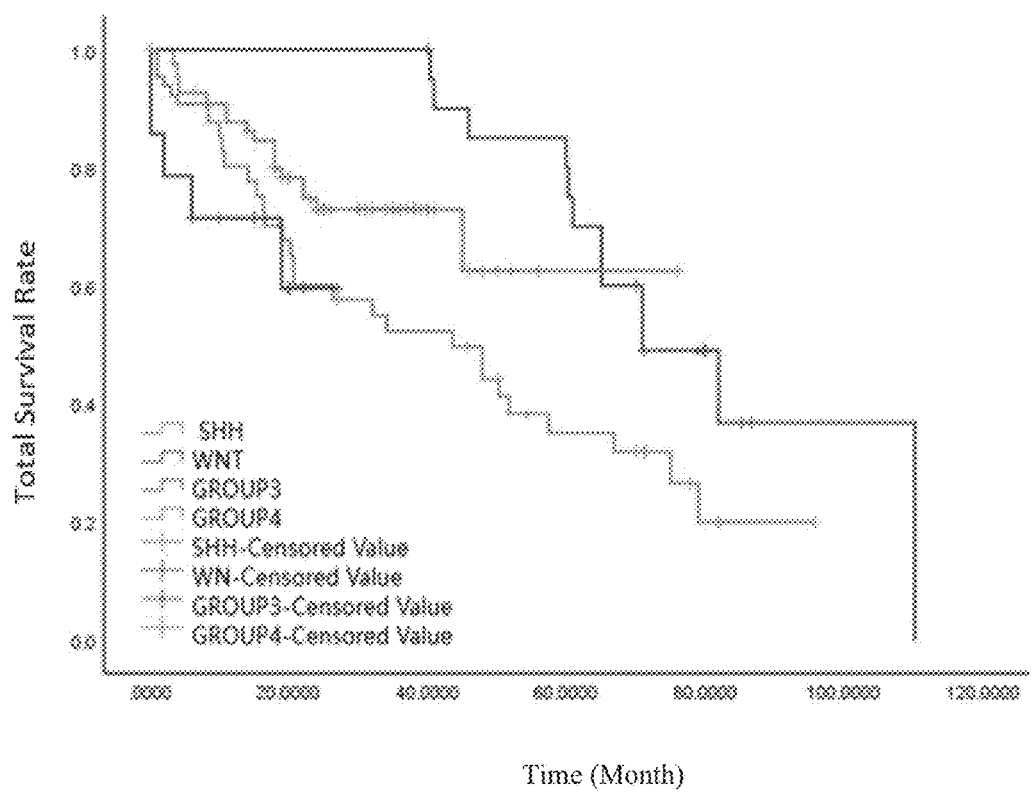
FIG. 2 is a schematic diagram of the total survival rates of different molecular subgroups of medulloblastoma with a significant difference in Example 7 of the present invention.
Figure 3:
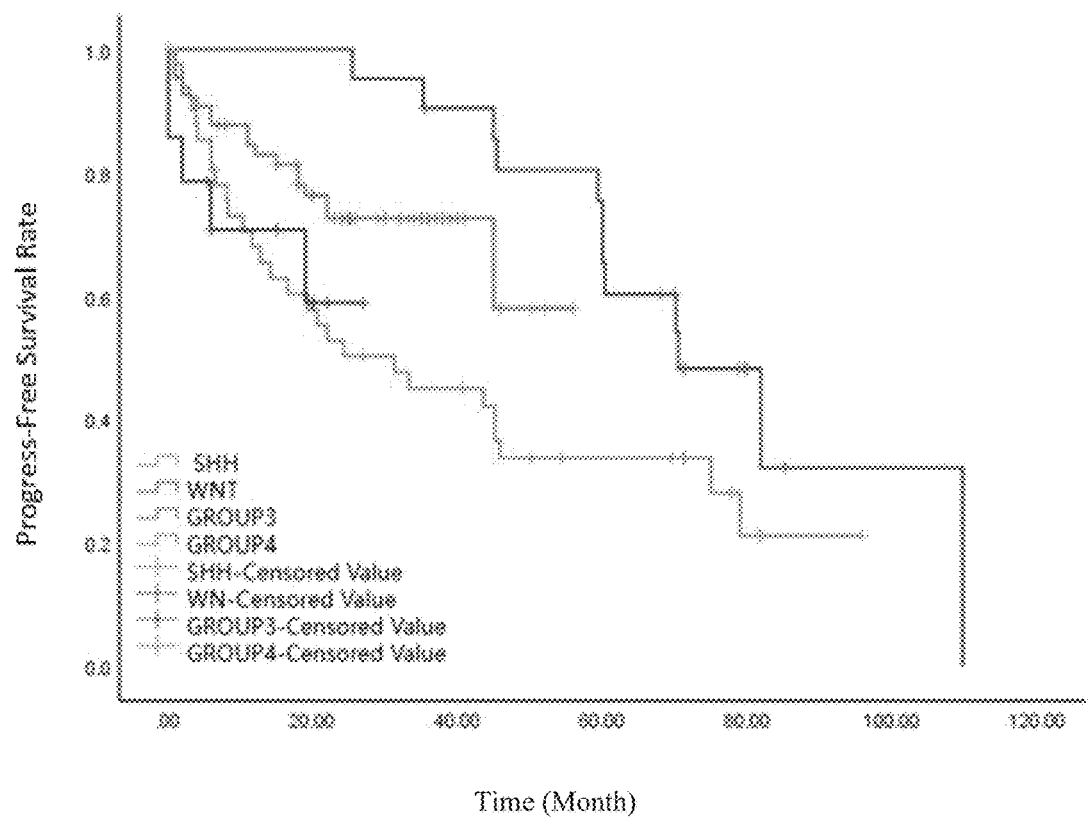
FIG. 3 is a schematic diagram of the progress-free survival rates with a significant difference between different molecular subgroups of medulloblastoma in Example 7 of the present invention.

142 samples were conducted classifying through 24 genes' statistical analysis model, among them, 21 were WNT subgroup, 29 were SHH subgroup, 11 were Group3 subgroup, and 64 were Group4 subgroup. The relationship between molecular classifying of medulloblastoma and the patient prognosis was analyzed by the Kaplan-Meier method. The results proved that the molecular classifying of medulloblastoma was significantly associated with the overall survival rate (FIG. 2). Among all patients, the 5-year overall survival rate was 85% for the WNT subgroup, 38% for the SHH subgroup, and 62% for the Group4 subgroup. The 5-year survival rate of the WNT subgroup was significantly better than that of other subgroups (P=0.027). In addition, this study further proved that medulloblastoma molecular classifying could also be used to evaluate progression-free survival rate (FIG. 3). Among all patients, the 5-year progression-free survival rate was 60% for the WNT subgroup, 36% for the SHH subgroup, and 60% for the Group4 subgroup. The 5-year progression-free survival rate of the WNT subgroup was also significantly better than that of other subgroups (P=0.034).

The above examples only express the mode of implementation of the present invention, and the description is relatively specific and detailed, but it shall not be construed as a limitation of the scope of the present invention. It should be noted that, for ordinary technicians in the field, a number of variations and improvements may be made without deviating from the conception of the present invention, which are within the protection scope of the present invention. Therefore, the protection scope of the present invention shall be subject to the attached claims.

What is claimed is:

1. A gene chip for identifying molecular subgroups of medulloblastoma, wherein the gene chip comprises:
a solid phase carrier and a probe, wherein the probe is hybridized with a set of genes comprising sequences of 13 genes to be tested and/or complementary sequences of the 13 genes, wherein the probe is as set forth in SEQ ID NOS. 49-61, respectively, wherein the set of genes comprises the following 13 genes: EPHA7 gene, OTX2 gene, ROBO1 gene, TTR gene, LGR5 gene, IGF2BP3 gene, TBR1 gene, ZFPM2 gene, TRDC gene, TRAC gene, PEX5L gene, NKD1 gene, and RALYL gene;
wherein the gene chip produces a result for identifying molecular subgroups of the medulloblastoma.

2. The gene chip according to claim 1, wherein the set of genes further comprises the following 11 genes: GABRA5 gene, GAD1 gene, TNC gene, KCNA1 gene, EOMES gene, MAB21L2 gene, WIF1 gene, DKK2 gene, PDLIM3 gene, IMPG2 gene, and KHDRBS2 gene.

3. A method of making the gene chip according to claim 1, comprising
screening the set of genes by the following method:
selecting gene combinations with a high specificity to the medulloblastoma by using an analysis technique of a big data and algorithm drive comprising the following steps:
building a medulloblastoma gene expression profile database, containing 20,250 genes, 461 samples, and 10 million data points;
correlating more than 20,000 human gene expression data in each of the 461 samples with clinical data of the 461 samples, screening specific medulloblastoma genes through a statistical analysis method variance test including analyzing a relevance of each of the specific medulloblastoma genes to medulloblastoma molecular subgroups, and extracting the specific medulloblastoma genes with a highest correlation as signature genes,
obtaining the 13 genes for constructing a classifying model, hybridizing a probe of the gene chip with a set of genes comprising sequences of the 13 genes to be tested and/or complementary sequences of the 13 genes.

4. A method for identifying molecular subgroups of medulloblastoma, comprising the step of using the gene chip according to claim 1 for the identifying of the molecular subgroups of the medulloblastoma; the method comprising the following steps:
providing the gene chip;
contacting biological samples containing tumor tissue with biomarkers;
determining an expression level of the biomarkers in the biological samples; and
detecting gene expression patterns in the biological samples using the gene chip and comparing with a gene expression profile database of medulloblastoma.

5. The method according to claim 4, wherein the set of genes hybridizing the probe of the gene chip further comprises the following 11 genes: GABRA5 gene, GAD1 gene, TNC gene, KCNA1 gene, EOMES gene, MAB21L2 gene, WIF1 gene, DKK2 gene, PDLIM3 gene, IMPG2 gene, and KHDRBS2 gene,
wherein the probe is hybridized with sequences of the 24 genes to be tested and/or complementary sequences of the 24 genes,
wherein the probe is as set forth in SEQ ID NOS. 49-72, respectively.

6. The method according to claim 3, wherein the set of genes hybridizing the probe of the gene chip further comprises the following 11 genes: GABRA5 gene, GAD1 gene, TNC gene, KCNA1 gene, EOMES gene, MAB21L2 gene, WIF1 gene, DKK2 gene, PDLIM3 gene, IMPG2 gene, and KHDRBS2 gene.

7. The method according to claim 4, wherein the set of genes hybridizing the probe of the gene chip further comprises the following 11 genes: GABRA5 gene, GAD1 gene, TNC gene, KCNA1 gene, EOMES gene, MAB21L2 gene, WIF1 gene, DKK2 gene, PDLIM3 gene, IMPG2 gene, and KHDRBS2 gene.

8. The method according to claim 4, wherein molecular subgroups of the medulloblastoma identifiable by the gene chip are WNT subgroup, SHH subgroup, Group3 subgroup, and Group4 subgroup.

* * * * *